United States Patent
Grosch et al.

(10) Patent No.: US 6,551,546 B1
(45) Date of Patent: Apr. 22, 2003

(54) METHOD FOR PRODUCING A SHAPED BODY USING A METAL OXIDE SOL

(75) Inventors: Georg Heinrich Grosch, Bad Dürkheim (DE); Ulrich Müller, Neustadt (DE); Michael Hesse, Worms (DE); Christian Lockemann, Mannheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/646,902

(22) PCT Filed: Apr. 7, 1999

(86) PCT No.: PCT/EP99/02355

§ 371 (c)(1),
(2), (4) Date: Oct. 10, 2000

(87) PCT Pub. No.: WO99/52626

PCT Pub. Date: Oct. 21, 1999

(30) Foreign Application Priority Data

Apr. 8, 1998 (DE) .......................... 198 15 879

Dec. 22, 1998 (DE) .......................... 198 59 561

(51) Int. Cl.$^7$ .......................... B28B 1/00; B29C 71/02
(52) U.S. Cl. .......................... 264/621; 264/232; 264/234
(58) Field of Search .......................... 264/621, 232, 264/234

(56) References Cited

FOREIGN PATENT DOCUMENTS

DE          19623611          * 12/1997

* cited by examiner

*Primary Examiner*—Christopher A. Fiorilla
(74) *Attorney, Agent, or Firm*—Oblon, Spivak, McClelland, Maier & Neustadt, P.C.

(57) ABSTRACT

A process for producing a shaped body comprising at least one porous oxidic material and at least one metal oxide comprises the following step (i):

(i) mixing the porous oxidic material or materials with at least one metal oxide sol which has a low content of alkali metal and alkaline earth metal ions and/or at least one metal oxide which has a low content of alkali metal and alkaline earth metal ions.

5 Claims, No Drawings

METHOD FOR PRODUCING A SHAPED BODY USING A METAL OXIDE SOL

This application is a 371 of PCT/EP99/02355 filed Apr. 7, 1999.

The present invention relates to a process for producing a shaped body comprising at least one porous oxidic material and at least one metal oxide, the shaped body per se and its use as catalyst in reactions of organic compounds, in particular for the epoxidation of organic compounds having at least one C—C double bond.

Shaped bodies which comprise porous oxidic materials are used in numerous chemical processes. This necessitates a production process which allows industrially relevant quantities of shaped bodies to be produced inexpensively.

To produce shaped bodies, the porous oxidic material is generally admixed with a binder, an organic viscosity-increasing substance and a liquid for making the mixture into a paste and is densified in a kneader or pan mill. The resulting mass is subsequently shaped by means of a ram extruder or screw extruder and the shaped bodies obtained are dried and calcined.

In order to produce shaped bodies which are also suitable for producing very reactive products, it is necessary to use chemically inert binders which prevent further reaction of these products.

Suitable binders are a series of metal oxides. Examples which may be mentioned are oxides of silicon, of aluminum, of titanium or of zirconium. Silicon dioxide as binder is disclosed, for example, in U.S. Pat. Nos. 5,500,199 and 4,859,785.

In such binders, the content of alkali metal and alkaline earth metal ions should be as low as possible, which is why it is necessary to use binder sources which are low in or free of alkali metals and alkaline earth metals.

To produce the abovementioned metal oxide binders, it is possible to use corresponding metal oxide sols as starting materials. In the preparation of, for example, the abovementioned silicon dioxide binders which are low in or free of alkali metals and alkaline earth metals, silica sol which is low in or free of alkali metal and alkaline earth metals is employed as binder source.

In the preparation of silica sols, it is possible to start from alkali metal silicates, but this generally leads to undesirably high contents of alkali metal ions in the silica sol. The preparation of such silica sols is described, for example, in "Ullmann's Encyclopedia of Industrial Chemistry", volume A 23 (1993), pp. 614–629.

JP-A-07 048 117 discloses the preparation of silica sol by hydrolysis of alkoxysilanes by means of ammonia in the presence of a large excess of alcohol; the silica sols obtained contain up to 10% by weight of silicon dioxide.

JP-A-05 085 714 describes the acid decomposition of alkoxysilanes, likewise in alcoholic medium. This gives silica sols having silicon dioxide contents of from 1 to 10% by weight.

A disadvantage of the processes for preparing silica sols disclosed in the latter two publications is the low silicon dioxide content which can be achieved in the silica sols. This makes the process uneconomical since plant capacity is wasted by excess water both in sol production and in further processing.

It is an object of the present invention to provide an industrially usable process for producing shaped bodies which have a low content of alkali metal and alkaline earth metal ions and can be used as catalysts, preferably in a fixed bed.

We have found that this object is achieved in a process for producing such shaped bodies by mixing porous oxidic material with metal oxide sol and/or metal oxide in a first step of the process, where the metal oxide sol and the metal oxide each have a low content of alkali metal and alkaline earth metal ions.

The present invention accordingly provides a process for producing a shaped body comprising at least one porous oxidic material and at least one metal oxide, which comprises the following step (i):

(i) mixing the porous oxidic material or materials with at least one metal oxide sol which has a low content of alkali metal and alkaline earth metal ions and/or at least one metal oxide which has a low content of alkali metal and alkaline earth metal ions.

The present invention likewise provides a shaped body which can be produced by the above-described process and has a content of alkali metal and alkaline earth metal ions of preferably less than 700 ppm, particularly preferably less than 600 ppm and in particular less than 500 ppm.

In a preferred embodiment of the process of the present invention, the metal oxide sol is prepared by hydrolysis of at least one metallic acid ester.

The present invention therefore also provides a process as described above in which the metal oxide sol is prepared by hydrolysis of at least one metallic acid ester.

The metallic acid esters employed for the hydrolysis can be purified prior to the hydrolysis. All suitable methods are conceivable here. Preference is given to subjecting the metallic acid esters to a distillation prior to the hydrolysis.

For the hydrolysis of the metallic acid ester, all possible methods can be used in principle. However, in the process of the present invention, the hydrolysis is preferably carried out in aqueous medium. This gives the advantage that, compared to hydrolyses known from the literature, for example from JP 07,048,117 or JP 05,085,714, in which an excess of alcohol is employed, significantly less alcohol has to be distilled off.

The hydrolysis can be catalyzed by addition of basic or acidic substances. Preference is given to basic or acidic substances which can be removed by calcination without leaving a residue. Particular preference is given to using substances selected from the group consisting of ammonia, alkylamines, alkanolamines, arylamines, carboxylic acids, nitric acid and hydrochloric acid. In particular, ammonia, alkylamines, alkanolamines and carboxylic acids are used.

The metallic acid esters used in the process of the present invention are preferably esters of orthosilicic acid.

In the process of the present invention, the hydrolysis of the metallic acid esters is carried out at from 20 to 100° C., preferably from 60 to 95° C., and at a pH of from 4 to 10, preferably from 5 to 9, particularly preferably from 7 to 9.

The molar ratio of catalytically active substance/metallic acid ester is generally from 0.0001 to 0.11, preferably from 0.0002 to 0.01 and in particular from 0.0005 to 0.008.

In the process of the present invention, the hydrolysis gives metal oxide sols, preferably silica sols, which have a content of alkali metal and alkaline earth metal ions of less than 800 ppm, preferably less than 600 ppm, more preferably less than 400 ppm, more preferably less than 200 ppm, more preferably less than 100 ppm, particularly preferably less than 50 ppm, more particularly preferably less than 10 ppm, in particular less than 5 ppm.

The present invention accordingly provides a metal oxide sol having a content of alkali metal and alkaline earth metal ions of less than 800 ppm which can be prepared by hydrolysis of at least one metallic acid ester.

The metal oxide content of the metal oxide sols prepared according to the present invention is generally up to 50% by weight, preferably from 10 to 40% by weight.

The alcohol formed in the hydrolysis is generally distilled off in the process of the present invention. However, small amounts of alcohol can remain in the metal oxide sol as long as they do not adversely affect the further steps of the process of the present invention.

An advantage for the industrial use of the metal oxide sols prepared according to the present invention is that they display no tendency to form gels. Specific precautionary measures for preventing gel formation are thus superfluous. The metal oxide sols prepared according to the present invention can be stored for a number of weeks, which makes coordination of the time at which they are prepared with further processing steps unproblematical.

In the process of the present invention, a mixture comprising at least one porous oxidic material and at least one metal oxide is prepared using a metal oxide sol prepared as described above as metal oxide source.

In principle, there are no restrictions in respect of the method of producing the mixture. However, in the process of the present invention, preference is given to spraying a suspension comprising at least one porous oxidic material and metal oxide sol.

Here, the amount of porous oxidic material present in the suspension is subject to no restrictions as long as the processability of the suspension during preparation and spraying is ensured. The weight ratio of porous oxidic material to the metal oxide of the metal oxide sol is preferably from 10 to 0.1, particularly preferably from 8 to 1.

The main constituents of the suspension are generally porous oxidic material, metal oxide sol and water. The suspension can additionally contain residual traces of organic compounds. These can originate, for example, from the preparation of the porous oxidic material. Likewise conceivable are alcohols which are formed in the hydrolysis of metallic acid esters or substances which are added as described above to promote the hydrolysis of metallic acid esters.

Depending on the moisture content wanted in the mixture for further processing, drying can follow. Here, all conceivable methods can be employed. Drying of the mixture is preferably carried out simultaneously with spraying in a spray drying step. The spray dryers are preferably operated using inert gases, particularly preferably nitrogen or argon.

As regards the porous oxidic materials which can be used in the process of the present invention for producing shaped bodies, there are no particular restrictions as long as it is possible to produce shaped bodies as described herein from these materials and as long as these materials have the necessary catalytic activity.

The porous oxidic material is preferably a zeolite. Zeolites are, as is known, crystalline aluminosilicates having ordered channel and cage structures and containing micropores. For the purposes of the present invention, the term "micropores" corresponds to the definition in "Pure Appl. Chem." 57 (1985), p. 603–619, and refers to pores having a pore diameter of less than 2 nm. The framework of such zeolites is built up of $SiO_4$ and $AlO_4$ tetrahedra which are connected via shared oxygen atoms. An overview of the known structures may be found, for example, in W. M. Meier, D. H. Olson and Ch. Baerlocher in "Atlas of Zeolite Structure Types", Elsevier, 4th Edition, London 1996.

There are also zeolites which contain no aluminum and in which the Si(IV) in the silicate lattice is partially replaced by titanium as Ti(IV). The titanium zeolites, in particular those having a crystal structure of the MFI type, and possible ways of preparing them are described, for example, in EP-A 0 311 983 and EP-A 0 405 978. Apart from silicon and titanium, such materials can further comprise additional elements such as aluminum, zirconium, tin, iron, niobium, cobalt, nickel, gallium, boron or small amounts of fluorine.

In the zeolites described, the titanium can be partially or completely replaced by vanadium, zirconium, chromium, niobium or iron or by a mixture of two or more thereof. The molar ratio of titanium and/or vanadium, zirconium, chromium, niobium or iron to the sum of silicon and titanium and/or vanadium, zirconium, chromium, niobium or iron is generally in the range from 0.01:1 to 0.1:1.

Titanium zeolites having an MFI structure are known for being able to be identified by means of a particular X-ray diffraction pattern and also by means of a lattice vibration band in the infrared (IR) region at about 960 $cm^{-1}$ and thus differing from alkali metal titanates or crystalline and amorphous $TiO_2$ phases.

Preference is given to using titanium, vanadium, chromium, niobium or zirconium zeolites, more preferably titanium zeolites and in particular titanium silicalites.

Specific examples are titanium, vanadium, chromium, niobium and zirconium zeolites having a pentasil zeolite structure, in particular the types assigned by X-ray crystallography to the BEA, MOR, TON, MTW, FER, MFI, MEL, CHA, ERI, RHO, GIS, BOG, NON, EMT, HEU, KFI, FAU, DDR, MTT, RUT, RTH, LTL, MAZ, GME, NES, OFF, SGT, EUO, MFS, MWW or MFI/MEL structure and also ITQ-4. Zeolites of this type are described, for example, in the abovementioned reference by Meier et al. Also conceivable for use in the process of the present invention are titanium-containing zeolites having the UTD-1, CIT-1 or CIT-5 structure. Further titanium-containing zeolites are those having the ZSM-48 or ZSM-12 structure.

Such zeolites are described, inter alia, in U.S. Pat.No. 5,430,000 and WO 94/29408, whose contents pertaining to this subject are fully incorporated by reference into the present application. In the process of the present invention, particular preference is given to Ti zeolites having an MFI, MEL or MFI/MEL structure.

Further preference is given to, specifically, the Ti-containing zeolite catalysts which are generally referred to as "TS-1", "TS-2", "TS-3", and also Ti zeolites having a framework structure isomorphous with β-zeolite.

The present invention accordingly provides a process for producing a shaped body as described above in which the porous oxidic material is a zeolite.

Of course, it is also possible to use mixtures of two or more porous oxidic materials, in particular those mentioned above, in the process of the present invention.

The abovementioned titanium, zirconium, chromium, niobium, iron and vanadium zeolites are usually prepared by reacting an aqueous mixture of a metal oxide source, preferably an $SiO_2$ source, and a titanium, zirconium, chromium, niobium, iron or vanadium source, e.g. titanium oxide or an appropriate vanadium oxide, zirconium alkoxide, chromium oxide, niobium oxide or iron oxide, and a nitrogen-containing organic base as template, e.g. tetrapropylammonium hydroxide, if desired with further addition of basic compounds, in a pressure vessel at elevated temperature for a number of hours or a few days to give a crystalline product. This is filtered off, washed, dried and calcined at elevated temperature to remove the organic nitrogen base. In the powder obtained in this way, at least some of the titanium or the zirconium, chromium, niobium, iron and/or vanadium is present within the zeolite framework in varying proportions with 4-, 5- or 6-coordination. To improve the catalytic properties, this can be followed by repeated washing with hydrogen peroxide solution acidified with sulfuric acid, after which the titanium or zirconium, chromium, niobium, iron and/or vanadium zeolite powder has to be dried and calcined again. The titanium or zirconium, chromium, niobium, iron or vanadium zeolite powder prepared in this way is used in the process of the present invention as a component of the above-described suspension.

In particular, the present invention therefore provides a process as described above in which the porous oxidic material or materials is mixed with at least one metal oxide sol, wherein the porous oxidic material or materials is prepared by a process which comprises one or more of the following steps (a) to (f):

(a) preparation of a preferably aqueous mixture of at least one metal oxide source, preferably an $SiO_2$ source, and a further metal source, for example a titanium, zirconium, chromium, niobium, iron or vanadium source, (b) crystallization of the mixture from (a) in a pressure vessel with addition of at least one template compound, if desired with addition of a further basic compound, (c) drying of the crystalline product present in the suspension resulting from (b), preferably by spray drying, (d) calcination of the dried product from (c), (e) comminution of the calcined product from (d), for example by milling, to give particles having particle sizes of less than 500 $\mu$m, preferably less than 300 $\mu$m, particularly preferably less than 200 $\mu$m, (f) if desired, repeated washing of the comminuted product from (e) with subsequent drying and calcination.

With regard to the pore structure of the porous oxidic materials, too, there are no particular restrictions, i.e. the material can have micropores, mesopores, macropores, micropores and mesopores, micropores and macropores, mesopores and macropores or micropores, mesopores and macropores, where the definition of the terms "mesopores" and "macropores" likewise corresponds to that in the above-mentioned reference in "Pure Appl. Chem." and relates to pores having a diameter of from>2 nm to about 50 nm and of>about 50 nm, respectively.

However, preference is given to using microporous oxidic materials such as titanium silicalites.

In a further preferred embodiment of the process of the present invention, the porous oxidic material or materials is mixed in step (i) with at least one metal oxide which has a low content of alkali metal and alkaline earth metal ions.

If the porous oxidic material is mixed with two or more metal oxides, it is possible to mix the porous oxidic material or materials with one metal oxide first and to mix the resulting mixture with a further metal oxide. If desired, this mixture can then be mixed with a further metal oxide. Likewise, it is also possible to mix the porous oxidic material with a mixture of two or more metal oxides.

The alkali metal and alkaline earth metal content of this metal oxide or the mixture of two or more metal oxides is generally less than 800 ppm, preferably less than 600 ppm, particularly preferably less than 500 ppm and in particular less than 200 ppm.

Such metal oxides having a low content of alkali metal and alkaline earth metal ions are, for example, pyrogenic metal oxides, for example pyrogenic silica.

Of course, it is also possible to use conventional metal oxides in the process of the present invention, with the proviso that their content of alkali metal and alkaline earth metal ions is appropriately low, as indicated above.

It is also possible, in the case of one or more conventional metal oxides which have a content of alkali metal and alkaline earth metal ions which is higher than that specified above, to lower the content of alkali metal and alkaline earth metal ions by washing, extraction or other suitable measures, likewise naturally by a combination of two or more suitable measures, to such an extent that the metal oxides can be used in the process of the present invention.

Depending on the measure employed for lowering the content of alkali metal and alkaline earth metal ions, it may be necessary to subject the conventional metal oxide or oxides to appropriate after-treatment. For example, if the content of alkali metal and alkaline earth metal ions of a conventional metal oxide is reduced by washing, it is sometimes necessary to dry the conventional metal oxide after washing before it is mixed with the porous oxidic material or materials.

In the process of the present invention, it is naturally also possible to mix the mixture resulting from mixing the porous oxidic material or materials with the metal oxide with at least one metal oxide sol which has a low content of alkali metal and alkaline earth metal ions. As regards the preparation of this mixture, there are in principle no restrictions, as in the case of the preparation of the mixture of porous oxidic material and metal oxide sol, as described above. However, preference is given to spraying a suspension comprising the mixture of the porous oxidic material or materials and the metal oxide or oxides and the metal oxide sol or sols. As regards the amount of porous oxidic material present in this suspension, there are no restrictions as long as, as described already above, the processability of the suspension is ensured.

Furthermore, it is naturally also possible, in the process of the present invention, to mix a mixture resulting from mixing at least one porous oxidic material with at least one metal oxide sol with at least one metal oxide which has a low content of alkali metal and alkaline earth metal ions. Here, mixing with the metal oxide or oxides can immediately follow the preparation of the mixture of the porous oxidic material or materials and the metal oxide sol or sols. Should, as already described above, drying be necessary after the preparation of the mixture of the porous oxidic material or materials and the metal oxide sol or sols, it is also possible to mix the metal oxide with the dried mixture after drying.

In the process of the present invention, it is likewise possible to mix the porous oxidic material or materials simultaneously with at least one metal oxide sol and at least one metal oxide.

The mixture obtained after one of the above-described embodiments of the invention is densified in a further stage of the process of the present invention. In this densification or shaping step, further metal oxide can, if desired, be introduced using a metal oxide sol prepared as described above as metal oxide source. This processing step can be carried out in all suitable apparatuses, although kneaders, pan mills or extruders are preferred. For industrial use of the process of the present invention, particular preference is given to using a pan mill.

If, according to an embodiment which has already been described above, a mixture of at least one porous oxidic material and at least one metal oxide is prepared first and this mixture is densified and metal oxide sol having a low content of alkali metal and alkaline earth metal ions is additionally added in the densification step, then, in a preferred embodiment of the present invention, from 20 to 80% by weight of porous oxidic material, from 10 to 60% by weight of metal oxide and from 5 to 30% by weight of metal oxide sol are used. Particular preference is given to using from 40 to 70% by weight of porous oxidic material, from 15 to 30% by weight of metal oxide and from 10 to 25% by weight of metal oxide sol. These percentages by weight are in each case based on the shaped body produced in the end, as described below. Preference is here given to using porous oxidic titanium-containing material and silica sol.

In a further embodiment of the process of the present invention, the mixing of the porous oxidic material or materials with the metal oxide or oxides having a low content of alkali metal and alkaline earth metal ions is carried out during the densification step. Accordingly, it is likewise possible to mix the porous oxidic material or materials, the metal oxide or oxides and additionally at least one metal oxide sol in the densification step.

In this shaping step it is also possible to add one or more viscosity-increasing substances as materials for making the mixture into a paste; these substances may serve, inter alia, to increase the stability of the uncalcined shaped body, as described below. For this purpose, it is possible to use all suitable substances known from the prior art. In the process of the present invention, water or mixtures of water with one or more organic substances, provided that they are miscible with water, are used for making the mixture into a paste. The materials used for making the mixture into a paste can be removed again during the later calcination of the shaped body.

Preference is given to using organic, in particular hydrophilic organic, polymers such as cellulose, cellulose derivatives, for example methylcellulose, ethylcellulose or hexylcellulose, polyvinylpyrrolidone, ammonium (meth) acrylates, Tylose or mixtures of two or more thereof. Particular preference is given to using methylcellulose.

As further additives, it is possible to add ammonium, amines or amine-like compounds such as tetraalkylammonium compounds or aminoalkoxides. Such further additives are described in EP-A 0 389 041, EP-A 0 200 260 and WO 95/19222, which in this respect are fully incorporated by reference into the present application.

Instead of basic additives, it is also possible to use acidic additives. Preference is given to organic acidic compounds which can be burned out by calcination after the shaping step. Particular preference is given to carboxylic acids.

The amount of these auxiliaries is preferably from 1 to 10% by weight, particularly preferably from 2 to 7% by weight, in each case based on the shaped body produced in the end, as described below.

To influence properties of the shaped body such as transport pore volume, transport pore diameter and transport pore distribution, it is possible to add further substances, preferably organic compounds, in particular organic polymers, as further additives which can also influence the shapeability of the composition. Such additives include alginates, polyvinylpyrrolidones, starch, cellulose, polyethers, polyesters, polyamides, polyamines, polyimines, polyalkenes, polystyrene, styrene copolymers, polyacrylates, polymethacrylates, fatty acids such as stearic acid, high molecular weight polyalkylene glycols such as polyethylene glycol, polypropylene glycol or polybutylene glycol, or mixtures of two or more thereof. The total amount of these materials, based on the shaped body produced in the end, as described below, is preferably from 0.5 to 10% by weight, particularly preferably from 1 to 6% by weight.

The present invention accordingly also provides for the use of polyalkylene glycol, in particular polyethylene glycol, in the production of shaped bodies comprising titanium silicalite, particularly those which are used as catalysts for selective oxidation.

In a preferred embodiment, the process of the present invention is used to produce shaped bodies which are essentially microporous but can additionally have mesopores and/or macropores. The pore volume of the mesopores and macropores in the shaped body of the present invention, determined in accordance with DIN 66133 by mercury porosimetry, is greater than 0.1 ml/g, preferably greater than 0.2 ml/g, particularly preferably greater than 0.3 ml/g, in particular greater than 0.5 ml/g.

The order of addition of the above-described additives to the mixture which has been obtained by one of the above-described methods is not critical. It is equally possible to introduce firstly further metal oxide via a metal oxide sol, subsequently the viscosity-increasing substances and then the substances which influence the transport properties and/or the shapeability of the densified composition or to imply any other order desired.

Prior to the densification, the generally still pulverulent mixture can, if desired, be homogenized in the kneader or extruder for from 10 to 180 minutes. This is generally carried out at a temperature in the range from about 10° C. to the boiling point of the material for making the mixture into a paste and at atmospheric pressure or slightly superatmospheric pressure. The mixture is kneaded until an extrudable mass has been formed.

The composition which has been obtained from the densification step and is now ready for shaping has, in the process of the present invention, a metal oxide content of at least 10% by weight, preferably at least 15% by weight, particularly preferably at least 20% by weight, in particular at least 30% by weight, based on the total composition. Particularly when using titanium-containing microporous oxides, the composition produced in the process of the present invention leads to no problems caused by thixotropic properties in the subsequent shaping step.

In principle, kneading and shaping can be carried out using all conventional kneading and shaping equipment or methods which are well known from the prior art and are suitable for producing, for example, shaped catalyst bodies.

Preference is given to using methods in which shaping is carried out by extrusion in customary extruders, for example to produce extrudates having a diameter of usually from about 1 to about 10 mm, in particular from about 1.5 to about 5 mm. Such extrusion equipment is described, for example, in "Ullmanns Enzyklopädie der Technischen Chemie", 4th edition, vol. 2 (1972), p. 295 ff. Apart from the use of a screw extruder, preference is likewise given to using a ram extruder. In the case of a large-scale industrial application of the process, particular preference is given to using screw extruders.

The extrudates are either extruded rods or honeycombs. The honeycombs can have any desired shape. They can be, for example, round extrudates, hollow extrudates or star-shaped extrudates. The honeycombs can also have any diameter. The external shape and the diameter are generally decided by process engineering requirements which are determined by the process in which the shaped bodies are to be used.

Before, during or after the shaping step, noble metals in the form of suitable noble metal components, for example in the form of water-soluble salts, can be applied to the material. Such a process is preferably employed to produce oxidation catalysts based on titanium silicates or vanadium silicates having a zeolite structure, making it possible to obtain catalysts which contain from 0.01 to 30% by weight of one or more noble metals selected from the group consisting of ruthenium, rhodium, palladium, osmium, iridium, platinum, rhenium, gold and silver. Such catalysts are described, for example, in DE-A 196 23 609.6 which is hereby, in respect of the catalysts described therein, fully incorporated by reference into the present application.

In many cases, however, it is most expedient to apply the noble metal components to the shaped bodies only after the shaping step, particularly when a high-temperature treatment of the catalyst comprising noble metal(s) is undesirable. The noble metal components can, in particular, be applied to the shaped body by ion exchange, impregnation or spraying-on. Application can be carried out using organic solvents, aqueous ammoniacal solutions or supercritical phases such as carbon dioxide.

The use of the above-described methods enables a wide variety of catalysts comprising noble metals to be produced. Thus, a type of coated catalyst can be produced by spraying the noble metal solution onto the shaped bodies. The thickness of this coating or shell comprising noble metal(s) can be significantly increased by impregnation, while in the case of ion exchange the catalyst particles are essentially uniformly loaded with noble metal across the entire cross section of the shaped body.

After extrusion by means of a ram extruder or a screw extruder, the shaped bodies obtained are dried for from about 1 to 20 hours at generally from 50 to 250° C., preferably from 80 to 250° C., at pressures of generally from 0.01 to 5 bar, preferably from 0.05 to 1.5 bar.

The subsequent calcination is carried out at from 250 to 800° C., preferably from 350 to 600° C., particularly preferably from 400 to 500° C. The pressure range employed is similar to that for drying. In general, the calcination is carried out in an oxygen-containing atmosphere, with the oxygen content being from 0.1 to 90% by volume, preferably from 0.2 to 22% by volume, particularly preferably from 0.2 to 10% by volume.

The present invention thus also provides a process for producing shaped bodies, as described above, which comprises the following steps (i) to (v):

(i) mixing the porous oxidic material or materials with at least one metal oxide sol which has a low content of alkali metal and alkaline earth metal ions and/or at least one metal oxide which has a low content of alkali metal and alkaline earth metal ions;

(ii) densifying the mixture from step (i), if desired with addition of metal oxide sol;

(iii) shaping the composition from step (ii);

(iv) drying the shaped bodies from step (iii);

(v) calcining the dried shaped bodies from step (iv). In a specific embodiment of the invention, the metal oxide sol is added to the suspension obtained from the step (b) described further above, the resulting suspension is dried, preferably by spray drying, and the resulting powder is calcined. The dried and calcined product can then be further processed as per step (iii).

Of course, the extrudates obtained can be further processed. All methods of comminution, for example by crushing or breaking the shaped bodies, are conceivable, as are further chemical treatments as, for example, described above. If comminution takes place, preference is given to producing granules or chips having a particle diameter of from 0.1 to 5 mm, in particular from 0.5 to 2 mm.

These granules or chips as well as shaped bodies produced in another way contain virtually no finer particles than those having a minimum particle diameter of about 0.1 mm.

The shaped bodies of the present invention or produced according to the present invention can be used as catalysts, in particular for catalytic conversion, especially for the oxidation of organic molecules. Examples of possible reactions are:

the epoxidation of olefins, e.g. the preparation of propene oxide from propene and $H_2O_2$ or from propene and mixtures which yield $H_2O_2$ in situ;

hydroxylations such as the hydroxylation of monocyclic, bicyclic or polycyclic aromatics to give monosubstituted, disubstituted or higher-substituted hydroxyaromatics, for example the reaction of phenol and $H_2O_2$ or of phenol and mixtures which yield $H_2O_2$ in situ to give hydroquinone;

the conversion of alkanes into alcohols, aldehydes and acids;

oxime formation from ketones in the presence of $H_2O_2$ or mixtures which yield $H_2O_2$ in situ and ammonia (ammonoximation), for example the preparation of cyclohexanone oxime from cyclohexanone;

isomerization reactions such as the conversion of epoxides into aldehydes;

and also further reactions described in the literature as being catalyzed by such shaped bodies, in particular zeolite catalysts, as are described, for example, by W. Hölderich in "Zeolites: Catalysts for the Synthesis of Organic Compounds", Elsevier, Stud. Surf. Sci. Catal., 49, Amsterdam (1989), pp. 69–93, and in particular for possible oxidation reactions as described by B. Notari in Stud. Surf. Sci. Catal., 37 (1987), pp. 413–425, or in Advances in Catalysis, vol. 41, Academic Press (1996), pp. 253–334.

The present invention therefore provides for the use of one of the shaped bodies produced as described above or a mixture of two or more thereof as a catalyst.

The zeolites which have been extensively discussed above are particularly suitable for the epoxidation of alkenes.

The present invention accordingly also provides a process for preparing at least one alkene oxide, which comprises the following step (III):

(III) reaction of at least one alkene with hydrogen peroxide over a catalyst which is a shaped body produced by a process as described above or a shaped body as described above.

Alkenes which are possibilities for such functionalization by epoxidation are, for example, ethene, propene, 1-butene, 2-butene, isobutene, butadiene, pentenes, piperylene, hexenes, hexadienes, heptenes, octenes, diisobutene, trimethylpentene, nonenes, dodecene, tridecene, tetra- to eicosenes, tri- and tetrapropene, polybutadienes, polyisobutenes, isoprene, terpenes, geraniol, linalool, linalyl acetate, methylenecyclopropane, cyclopentene, cyclohexene, norbomene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

The zeolites which have been extensively discussed above are particularly suitable for the epoxidation of alkenes having from 2 to 8 carbon atoms, more preferably ethene, propene or butene and in particular propene, to give the corresponding alkene oxides.

Accordingly, the present invention provides, in particular, for the use of the shaped body described herein as catalyst for preparing propene oxide starting from propene and hydrogen peroxide or from propene and mixtures which yield $H_2O_2$ in situ.

In a specific embodiment of the process, the alkene to be epoxidized is prepared by dehydrogenation of the corresponding alkane.

Accordingly, the present invention also provides a process as described above which comprises the additional step (I):

(I) preparation of the alkene or alkenes reacted in step (III) by dehydrogenation of at least one alkane.

This dehydrogenation can, in principle, be carried out by all methods known from the prior art. Such methods are described, inter alia, in EP-A 0 850 936 which in this respect is fully incorporated by reference into the present application.

In a preferred embodiment of the process of the present invention, the hydrogen which is generated in the dehydrogenation of the alkane or alkanes is used for preparing the hydrogen peroxide with which the alkene or alkenes produced in the dehydrogenation is reacted in step (III).

Accordingly, the present invention also provides a process as described above which comprises the following step (II):

(II) reaction of the hydrogen formed in step (I) to give hydrogen peroxide, where the hydrogen peroxide is used for the reaction in step (III).

The present invention accordingly also provides an integrated process for preparing an alkene oxide which comprises the steps (A) to (C):

(A) dehydrogenation of an alkane to give an alkene and hydrogen, (B) reaction of the hydrogen obtained in (A) to give hydrogen peroxide, and (C) reaction of the hydrogen peroxide from (B) with the alkene from (A) to give the alkene oxide using a shaped body according to the present invention.

The reaction of the hydrogen to give hydrogen peroxide can be carried out by all methods which are known from the prior art. In particular, the hydrogen can be reacted with molecular oxygen to give hydrogen peroxide. It is likewise conceivable to prepare hydrogen peroxide using the hydrogen from step (A) by means of the anthraquinone process. In both cases, it may be necessary to purify the hydrogen from step (A) before further use. Preference is, however, given to using the anthraquinone process. This is based on the catalytic hydrogenation of an anthraquinone compound to give the corresponding anthrahydroquinone compound, subsequent reaction of this with oxygen to form hydrogen peroxide and subsequent isolation of the hydrogen peroxide formed by extraction. The catalysis cycle is closed by rehydrogenation of the anthraquinone compound which is obtained back in the reaction with oxygen. An overview of the anthraquinone process is given in "Ullmann's Encyclopedia of Industrial Chemistry", 5th edition, volume 13, pages 447 to 456.

When using one or more shaped bodies produced according to the present invention as catalyst, the latter can, when deactivated, be regenerated by a process in which the regeneration is carried out by targeted burning-off of the deposits responsible for deactivation. This is preferably carried out in an inert gas atmosphere containing precisely defined amounts of substances which act as an oxygen source. This regeneration process is described in DE-A 197 23 949.8, the relevant content of which are fully incorporated by reference into the present application.

In addition, the present invention in its most general embodiment provides for the use of a metal oxide sol prepared as described above as binder for producing a shaped body having high chemical resistance and mechanical strength.

The following examples illustrate the invention.

EXAMPLES

Example 1

Preparation of a Microporous Oxidic Material 910 g of tetraethyl orthosilicate were placed in a four-neck flask (4 l capacity) and 15 g of tetraisopropyl orthotitanate were added from a dropping funnel over a period of 30 minutes while stirring (250 rpm, blade stirrer). A colorless, clear mixture was formed. 1600 g of a 20% strength by weight tetrapropylammonium hydroxide solution (alkali metal content<10 ppm) were subsequently added and the mixture was stirred for another 1 hour. The alcohol mixture formed by the hydrolysis (about 900 g) was distilled off at 90–100° C. 3 l of water were added and the now slightly opaque sol was transferred to a 5 l capacity stirring autoclave made of stainless steel.

The closed autoclave (anchor stirrer, 200 rpm) was brought to a reaction temperature of 175° C. at a heating rate of 3° C./min. The reaction was complete after 92 hours. The cooled reaction mixture (white suspension) was centrifuged and the solid was washed a number of times with water until neutral. The solid obtained was dried at 110° C. for 24 hours (weight: 298 g). The template remaining in the zeolite was subsequently burned off in air at 550° C. for 5 hours (calcination loss: 14% by weight).

The pure white product had, according to wet chemical analysis, a Ti content of 1.5% by weight and a residual alkali metal content of less than 100 ppm. The yield based on silicon dioxide used was 97%. The crystalites had a size of from 0.05 to 0.25 μm and the product displayed a typical band at about 960 cm$^{-1}$ in the IR spectrum.

Example 2

Preparation of a Silica Sol 3 l of water were placed in a 10 l four-neck flask provided with stirrer, thermometer and reflux condenser. The pH of the solution was adjusted to 8-9 using 6 g of 25% strength ammonia. The water was subsequently heated to 50° C. and 1300 g of tetraethyl orthosilicate were added from a dropping funnel.

The mixture of water and tetraethyl orthosilicate was refluxed for 3 hours. A further 1304 g of tetraethyl orthosilicate were then added via a dropping funnel. After refluxing for another 2 hours, the resulting silica sol/water mixture was stirred for a further 12 hours and the ethanol formed by hydrolysis was then distilled off.

The 3618 g of silica sol produced in this way had a silicon dioxide content of about 20% by weight and a content of alkali metal ions of less than 3 ppm.

Example 3

Preparation of a Silica Sol 188.6 g of water were placed in a 500 ml four-neck flask provided with stirrer, thermometer and reflux condenser. The pH of the solution was adjusted to 9 using 0.3 g of 25% strength ammonia. The water was subsequently heated to 50° C. and 111.65 g of tetraethyl orthosilicate were added from a dropping funnel.

The mixture of water and tetraethyl orthosilicate was refluxed for 2 hours. A further 111.65 g of tetraethyl orthosilicate were then added via a dropping funnel. After refluxing for another 2 hours, the resulting silica sol/water mixture was refluxed for another 12 hours. 50 g of water were subsequently added and the ethanol formed by hydrolysis was then distilled off.

The 169 g of silica sol produced in this way had a silicon dioxide content of about 38% by weight and a content of alkali metal ions of less than 5 ppm.

Example 4
Spraying of Titanium Silicalite 200 g of milled catalyst, prepared as described in Example 1, were first finely milled to a particle size of <300 µm and then suspended in 2000 g of water. 245 g of aqueous silica sol having a silicon dioxide content of 18% by weight, prepared as described in Example 2, were subsequently mixed in.

While stirring continually, the suspension was pumped by means of a peristaltic pump into a laboratory spray dryer made of glass (diameter: 200 mm, height of the cylindrical section: 500 mm) and atomized by means of a two-fluid nozzle (diameter of the liquid feed line: 2.5 mm, admission pressure of gas to nozzle: 3 bar).

In the spray dryer, the suspension was dried by means of the drying gas (nitrogen, throughput: 24 kg/h, inlet temperature: 210° C., outlet temperature: 100° C.) to give a fine, intimately mixed powder which was then separated out in a glass cyclone. The yield was 80%.

Example 5
Spraying of Titanium Silicalite 16.1 kg of catalyst, prepared as described in Example 1, were first coarsely milled in a hammer mill and then finely milled to a particle size of <300 µm using an impeller breaker.

The powder was subsequently suspended in 160 l of water with addition of 16 kg of aqueous silica sol having a silicon dioxide content of 20% by weight, prepared as described in Example 2, and placed in an open stirred vessel. While stirring continually, the suspension was taken off by means of a large peristaltic pump and dried in a spray drying unit (from Niro) to give a fine, intimately mixed powder.

The suspension was atomized using an atomizer disk with ceramic bushes (rotational speed: 17,000 rpm). Drying was carried out at an air inlet temperature of 260° C. and an air outlet temperature of 110° C.

The product was separated off from the stream of air in a cyclone. The yield was 13 kg.

Comparative Example 1
Shaping of Titanium Silicalite (Catalyst A)

Catalyst A was produced by mixing 1665 g of a spray-dried powder consisting of 89% by weight of a catalyst prepared as described in Example 1 and 11% by weight of silicon dioxide with 416 g of a silica sol having a silicon dioxide content of about 50% by weight (Ludox™ from DuPont). The spray-dried powder specified was prepared as described in Example 4 except that a commercially produced silica sol (Ludox AS-40 from DuPont) having a sodium content of 800 ppm was used in place of the silica sol prepared according to the present invention.

The mixture was made extrudable by addition of water and the extrusion aid methylcellulose and was extruded to give extrudates having a diameter of 1.5 mm.

These extrudates were dried at 120° C. and heated at 500° C. for 5 hours. The silicon dioxide binder content of the shaped body was 20% by weight, the sodium content was 700 ppm.

Comparative Example 2
Shaping of Titanium Silicalite (Catalyst B)

Catalyst B was produced by mixing 3000 g of a spray-dried powder consisting of 78% by weight of a catalyst prepared as described in Example 1 and 22% by weight of silicon dioxide with 750 g of a silica sol having a silicon dioxide content of about 43% by weight (Ludox AS-40 from DuPont).

The spray-dried powder specified was prepared as described in Example 4 except that a commercially produced silica sol (Ludox AS-40 from DuPont) having a sodium content of 800 ppm was used in place of the silica sol prepared according to the present invention.

The mixture was made extrudable by addition of water and the extrusion aid methylcellulose and was extruded to give extrudates having a diameter of 2.5 mm.

These extrudates were dried at 120° C. and heated at 500° C. for 5 hours. The silicon dioxide binder content of the shaped body was 30% by weight, the sodium content was 910 ppm. The lateral compressive strength of the extrudates was 37.9 N, the cutting resistance was 10.25 N.

Comparative Example 3
Shaping of Titanium Silicalite (Catalyst C)

Catalyst C was produced by mixing 7500 g of a spray-dried powder consisting of 78% by weight of a catalyst prepared as described in Example 1 and 22% by weight of silicon dioxide with 4300 g of a silica sol having a silicon dioxide content of about 43% by weight (Ludox AS-40 from DuPont) in a pan mill.

The spray-dried powder specified was prepared as described in Example 4 except that a commercially produced silica sol (Ludox AS-40 from DuPont) having a sodium content of 800 ppm was used in place of the silica sol prepared according to the present invention.

The mixture was made extrudable by addition of water and the extrusion aid methylcellulose and was extruded to give extrudates having a diameter of 1.5 mm.

These extrudates were dried at 120° C. and heated at 500° C. for 5 hours. The silicon dioxide binder content of the shaped body was 30% by weight, the sodium content was 900 ppm.

Example 6
Shaping of Titanium Silicalite (Catalyst D)

Catalyst D was produced by mixing 2200 g of a spray-dried powder consisting of 75% by weight of a catalyst prepared as described in Example 1 and 25% by weight of silicon dioxide with 1037 g of a silica sol having a silicon dioxide content of about 21% by weight, prepared as described in Example 2. The spray-dried powder specified was prepared by a method analogous to Example 4.

The mixture was made extrudable by addition of water and the extrusion aid methylcellulose and was extruded to give extrudates having a diameter of 1.5 mm.

These extrudates were dried at 120° C. and heated at 500° C. for 5 hours. The silicon dioxide binder content of the shaped body was 32% by weight, the sodium content was 400 ppm.

Example 7
Shaping of Titanium Silicalite (Catalyst E)

Catalyst E was produced by mixing 9700 g of a spray-dried powder consisting of 75% by weight of a catalyst prepared as described in Example 1 and 25% by weight of silicon dioxide with 13000 g of a silica sol having a silicon dioxide content of about 19% by weight, prepared as described in Example 2, in a pan mill.

The spray-dried powder specified was prepared by a method analogous to Example 4.

The mixture was made extrudable by addition of water and the extrusion aid methylcellulose and was extruded to give extrudates having a diameter of 1.5 mm.

These extrudates were dried at 120° C. and heated at 500° C. for 5 hours. The silicon dioxide binder content of the shaped body was 40% by weight, the sodium content was 420 ppm.

Example 8
The Shaping of Titanium Silicalite (Catalyst F)

Catalyst F was produced by mixing 8000 g of a spray-dried powder consisting of 70% by weight of a catalyst prepared as described in Example 1 and 30% by weight of silicon dioxide with 4000 g of a silica sol having a silicon dioxide content of about 19% by weight, prepared as described in Example 2, in a pan mill.

The spray-dried powder specified was prepared by a method analogous to Example 4.

The mixture was made extrudable by addition of water and the extrusion aid methylcellulose and was extruded to give extrudates having a diameter of 1.5 mm.

These extrudates were dried at 120° C. and heated at 500° C. for 5 hours. The silicon dioxide binder content of the shaped body was 40% by weight, the sodium content was 400 ppm. The cutting resistance was 2 N and the lateral compressive strength was 19 N.

Example 9
Densification and Shaping of Titanium Silicalite (Catalyst G)

3.5 kg of TS-1, prepared as described in Example 1, were densified in a pan mill with 1.23 kg of Aerosil® (DEGUSSA), 6.26 kg of silica sol prepared as described in Example 2 and 237 g of methylcellulose (Walocel®) for 60 minutes.

Subsequently 48 g of polyethylene glycol (ALKOX-E160®) were added, the mixture was densified for a further 30 minutes, 96 g of polyethylene glycol (ALKOX-E160®) and 450 g of deionized water were added and the mixture was once more densified for 15 minutes.

The shapeable composition was shaped by means of an extruder to give 1.5 mm round extrudates. The extrusion pressure was from 85 to 100 bar and the extrusion time was 15 minutes. These extrudates were dried at 120° C. and calcined at 500° C. in air for 5 hours.

The yield was 5.1 kg. The silicon dioxide binder content of the shaped body was 40% by weight, the sodium content was 500 ppm, the lateral compressive strength was 17 N and the macropore volume was 0.70 g/ml, determined by Hg porosimetry in accordance with DIN 66133.

Example 10
Catalytic Trial (Batch Operation)

In each case, an amount of catalyst A to G corresponding to a mass of titanium silicalite of 0.5 g was placed in a steel autoclave provided with a basket insert and sparging stirrer.

The autoclave was charged with 100 g of methanol, closed and checked for absence of leaks. The autoclave was subsequently heated to 40° C. and 11 g of liquid propene were metered into the autoclave.

9.0 g of a 30% strength by weight aqueous hydrogen peroxide solution were then pumped into the autoclave by means of an HPLC pump and the remaining hydrogen peroxide in the feed lines was subsequently rinsed into the autoclave using 16 ml of methanol. The initial hydrogen peroxide content of the reaction solution was 2.5% by weight.

After a reaction time of 2 hours, the autoclave was cooled and vented. The liquid product was analyzed cerimetrically for hydrogen peroxide. The propylene oxide content of the product was determined by gas chromatography.

The results of the analysis are summarized in the following table.

TABLE for Example 10 (Catalyst trial)

| Catalyst | Propylene oxide content of product % by weight | Hydrogen peroxide content of product % by weight |
| --- | --- | --- |
| A (comparative) | 0.88 | 1.72 |
| B (comparative) | 0.86 | 1.74 |
| C (comparative) | 0.93 | 1.51 |
| D | 1.39 | 1.28 |
| E | 1.47 | 1.19 |
| F | 1.34 | 1.25 |
| G | 1.1 | 1.45 |

Example 11
Catalytic Test (Continuous Operation)

24 g/h of hydrogen peroxide (40% by weight), 57 g/h of methanol and 11.7 ml/h of propene were passed at a reaction temperature of 40° C. and a pressure of 20 bar through a tube reactor charged with 28.1 g of the catalyst F according to the present invention.

After leaving the reactor, the reaction mixture was depressurized against atmospheric pressure in a Sambay evaporator. The low boilers which were separated off were analyzed on-line in a gas chromatograph. The liquid reaction product was collected, weighed and likewise analyzed by gas chromatography.

The total reaction time was 550 hours. During this time, the hydrogen peroxide conversion was far above 90%. The selectivity of hydrogen peroxide to propylene oxide was likewise significantly more than 90% over the total period of time.

Example 12
Catalytic Test (Continuous Operation)

9 g/h of hydrogen peroxide (40% by weight), 49 g/h of methanol and 8 g/h of propene were passed at a reaction temperature of 40° C. and a pressure of 20 bar through a tube reactor charged with 20 g of the catalyst G according to the present invention.

After leaving the reactor, the reaction mixture was depressurized against atmospheric pressure in a Sambay evaporator. The low boilers which were separated off were analyzed on-line in a gas chromatograph. The liquid reaction product was collected, weighed and likewise analyzed by gas chromatography.

The total reaction time was 850 hours. During this time, the hydrogen peroxide conversion was far above 90%. The selectivity of hydrogen peroxide to propylene oxide was likewise significantly more than 90% over the total period of time.

We claim:
1. A process for producing a shaped body comprising at least one porous oxidic material and at least one metal oxide, said process comprising

(i) mixing the porous oxidic material or materials with at least one metal oxide sol which has a low content of alkali metal and alkaline earth metal ions and/or at least one metal oxide which has a low content of alkali metal and alkaline earth metal ions.

(ii) densifying the mixture from step (i), (iii) shaping the composition from step (ii), (iv) drying the shaped body from step (iii), wherein the metal oxide sol has a content of alkali metal and alkaline earth metal ions of less than 10 ppm.

2. A process as claimed in claim 1 further comprising (v) calcining the dried shaped body from step (iv).

3. A process as claimed in claim 1, wherein the at least one metal oxide sol is prepared by hydrolysis of at least one metallic acid ester.

4. A process as claimed in claim 3, wherein the metallic acid ester or esters is an ester of orthosilicic acid.

5. A process as claimed in claim 1, wherein the porous oxidic material is a zeolite.

\* \* \* \* \*